US00PP30157P2

(12) United States Plant Patent
Horvath

(10) Patent No.: US PP30,157 P2
(45) Date of Patent: Jan. 29, 2019

(54) ***HOSTA* PLANT NAMED 'HASTA MAÑANA'**

(50) Latin Name: ***Hosta* hybrid**
Varietal Denomination: Hasta Mañana

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 22 days.

(21) Appl. No.: 15/530,116

(22) Filed: Dec. 5, 2016

(51) Int. Cl.
*A01H 5/12* (2018.01)

(52) U.S. Cl.
USPC ..... Plt./353

(58) Field of Classification Search
USPC ..... Plt./353

CPC ..... A01H 5/02; A01H 5/0272; A01H 5/12; A01H 5/00; A01H 6/56; A01H 6/12
See application file for complete search history.

(56) References Cited

PUBLICATIONS

Missouri Botanical Garden *Hosta* 'Hasta Manana' retrieved on Dec. 14, 2017, retrieved from the Internet at http://www.missouribotanicalgarden.org/PlantFinder/PlantFinderDetails.aspx?taxonid=371957&isprofile=0&%3B, 2 pp. (Year: 2017).*

* cited by examiner

*Primary Examiner* — June Hwu

(57) ABSTRACT

A new, distinct *Hosta* hybrid plant as shown and described, characterized by a light green RHS color 145 A immature foliage edged in RHS 155 A maturing to RHS color 162 C with age and having leaf edges with streaks of green 146 C and white 155 A.

2 Drawing Sheets

Latin name: *Hosta* hybrid.
Cultivar name: 'Hasta Mañana'.

BACKGROUND OF THE INVENTION

The present invention relates to a new and distinct cultivar of *Hosta* plant, botanically known as *Hosta* hybrid cultivar name, 'Hasta Mañana'. The new *Hosta* was discovered as a naturally occurring whole plant mutation of the non-patented *Hosta* cultivar, 'Francee', in April 2010 in amongst outdoor container plants at a nursery in Hebron, Ill., United States of America. Asexual reproduction of the new cultivar by division in 2011 at Hebron, Ill. has shown that the unique features of this new *Hosta* plant are stable and reproduced true to type in successive generations of asexual reproduction.

SUMMARY OF THE INVENTION

Plants of the cultivar 'Hasta Mañana' have not been observed under all possible environmental and cultural conditions. The phenotype may vary with changes in environmental conditions such as temperature, light intensity, day length, amount and frequency of irrigation and/or fertilizer rate, without any variance in genotype.

The following traits have been repeatedly observed and are determined to be unique characteristics of 'Hasta Mañana'. These characteristics in combination distinguish the *Hosta* as a new and unique cultivar. 1. Immature, new leaves emerge 145 A edged in 155 A. 2. As the leaves mature they become 162 C in the center and edged in both 155 A and 164 C. The new *Hosta* can be compared to its parent cultivar, 'Francee', not patented. 1. Plants of the new *Hosta* emerge lighter green and turn gold compared to the green foliage of the parent. 2. The variegated edge on the new *Hosta* can have two colors of green and white while the parent plant has only a thin white edge.

DESCRIPTION OF PHOTOGRAPHS

The accompanying colored photographs illustrate the overall appearance of the new *Hosta*, showing the colors as true as it is reasonably possible to obtain in color reproductions of this type. Colors in the photographs may differ slightly from the color value cited in the detailed botanical description, which accurately describe the actual colors in the new *Hosta*.

Figure 1:
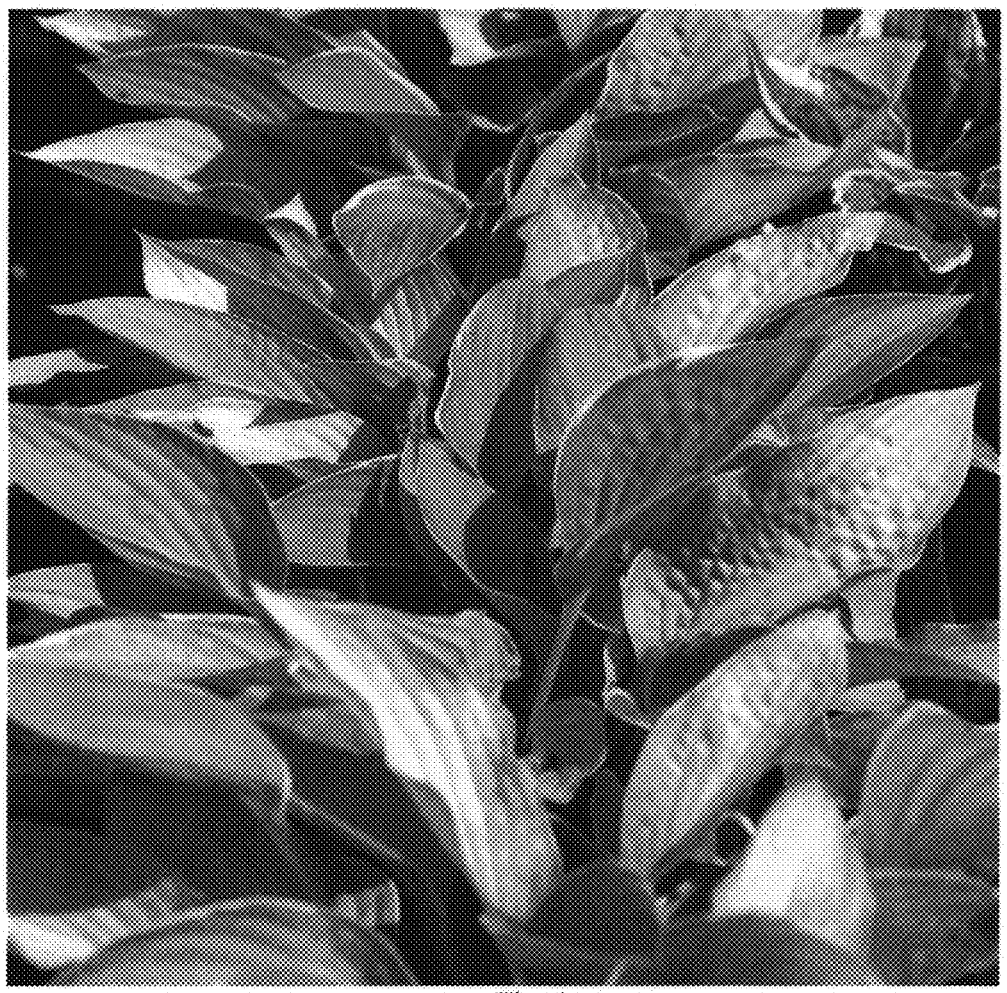

FIG. 1. Shows the plant in June with both new, immature leaves of green and maturing leaves turning gold.

Figure 2:
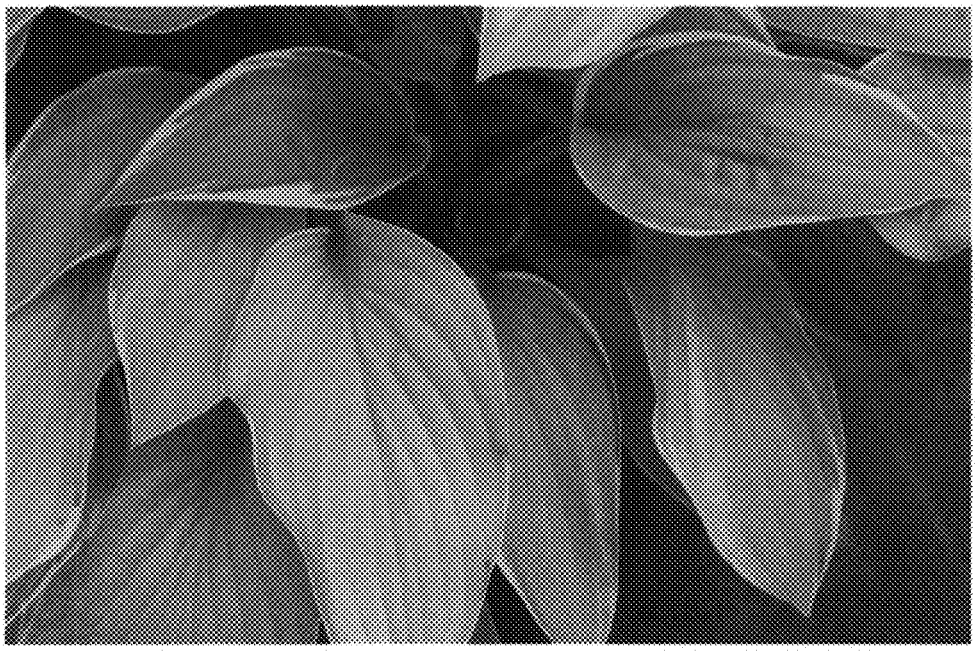

FIG. 2. Shows a close-up photograph in July with both new, immature leaves of green and maturing leaves turning gold.

Figure 3:
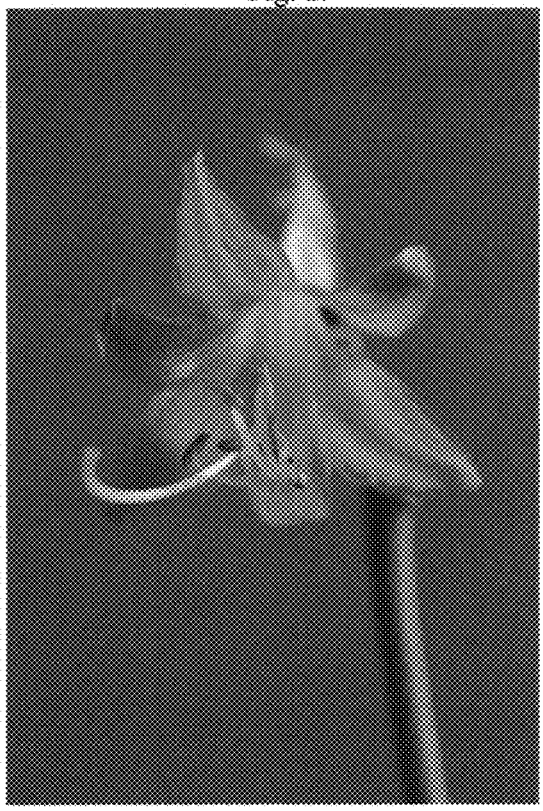

FIG. 3. Shows the flower.

DETAILED BOTANICAL DESCRIPTION

In the following description, color references are made to The Royal Horticultural Society Colour Chart (2001) except where general terms of ordinary dictionary significance are used. The following observations and measurements describe four-year old plants, as depicted in the accompanying color photographs, which were grown outdoors in plastic containers in Hebron, Ill. USA. Measurements and numerical values represent averages of typical plants.

Botanical classification: *Hosta* hybrid cultivar 'Hasta Mañana'.

Parentage: Naturally occurring whole plant mutation of *Hosta* cultivar 'Francee'.

Propagation: By division.

Plant description: The new *Hosta* is an open mound, dome-shaped, initially upright when young, leaves becoming outwardly arching.

*Culture*.—Light to medium shade in moist soil.

*Plant type*.—Herbaceous Perennial.

*Plant height*.—30 cm from the soil level and up to 87 cm to the top with the flower.

*Plant diameter*.—60 cm.

*Vigor and growth rate*.—Moderate.

*Disease resistance*.—No known particular resistance or susceptibility to disease.

Foliage: Leaves basal, simple and generally symmetrical.

*Leaf shape*.—Broadly ovate to ovate.

*Apex*.—Acute.

*Base*.—Rounded to cordate.

*Leaf margin*.—Entire.

*Leaf texture*.—Glabrous above and below, moderate substance.

*Leaf bulging*.—Weak to moderate. Leaf Blistering: weak to moderate.

*Leaf size*.—The blade is 16 cm in length, while the entire leaf with the petiole is 43 cm.

*Leaf width*.—About 9 cm.

*Venation pattern*.—Campylodrome with 8 pairs of veins.

*Leaf color*.—Early season foliage; Upper surface of leaf center: 145 A. Lower surface of the leaf center: 145 B margins being up to 2 cm wide on upper and lower surface: mostly 155 A but also having 146 C. Mid. to late season foliage; Upper surface of Leaf center: 162 C. Lower surface of the leaf center: 158 B. Bi-colored margins on upper and lower surface: Streaks of 155 A and 146 C.

Petiole:

*Length*.—27 cm. Diameter: 1 cm.

*Color*.—Upper surface of both new and mature foliage: 145 A, Lower Surface: 145 A on the edge and 145 C in the center.

Bud:

*Shape*.—Balloon-shaped increases in size until day before opening.

*Length*.—Up to 42 mm.

*Diameter*.—About 11 mm.

*Color*.—Light lavender base 85 A, tips 85 D.

Flower:

*Blooms*.—Mid-July to mid-August in Hebron, Ill.

*Fragrance*.—None observed.

*Arrangement*.—Raceme of numerous single flowers comprised of six tepals. There is one raceme per plant. The number of flowers per raceme is about 20 with each flower lasting approximately one day.

*Shape*.—Funnel-shaped.

*Size*.—Length about 42 mm, diameter 25 mm.

*Color*.—Light lavender, about 85 D with the midrib of the tepals lavender, N88 C.

Perianth: Arrangement; Three interior and three exterior tepals; fused. Corolla tube outer color 85 D.

*Tepal length*.—42 mm. Tepal width: 11 mm.

*Tepal color*.—Upper surface, Light lavender 85 D with tepal midrib lavender, N88 C; Lower surface, light lavender about 85 D midrib lavender N88 C. The tepals are ovate in shape with an acute apex. Margin is often transparent on the interior tepals, less so or not transparent on exterior tepals. Tepals are ribbed.

Floral bracts: Arrangement at pedicel base. There is one bract per flower.

*Length*.—About 13 mm. Width: About 5 mm.

*Shape*.—Lanceolate, keel-shaped.

*Color*.—At base N82 D.

Pedicel:

*Length*.—About 3 mm.

*Angle*.—Horizontal to about 100 degrees from vertical; bent with the weight of the flower. Color: 145 A.

Scape:

*Length*.—87 cm, Width: 5 mm.

*Aspect*.—Upright texture; smooth, glaucous.

*Color*.—Green 146 D.

Reproductive organs:

*Stamens*.—Quantity: Six dorsifixed.

*Filament length*.—About 50 mm. Filament color: Between 145 B and D.

Anthers:

*Size*.—About 3 mm by 1 mm. Color: Yellow 157 A.

Pollen:

*Amount*.—Moderate. Color: Yellow 157 A.

Pistils: Quantity—One.

*Length*.—About 52 mm.

*Style length*.—About 40 mm. Style Color: Between 145 B and D.

*Stigma color*.—Between 145 B and D.

*Ovary length*.—About 6 mm. Ovary Color: Between 145 B and D.

Seed development: None. Fruit none.

Root development: Fleshy, typically 3 mm in diameter and 30 to 40 cm in length.

I claim:

1. A new, distinct *Hosta* hybrid plant as shown and described, characterized by a light green RHS color 145 A immature foliage edged in RHS 155 A maturing to RHS color 162 C with age and having leaf edges with streaks of green 146 C and white 155 A compared to the parent.

* * * * *